United States Patent
Iglesia et al.

(10) Patent No.: US 6,647,342 B2
(45) Date of Patent: Nov. 11, 2003

(54) KNOWLEDGE-BASED PROCESS FOR THE DEVELOPMENT OF MATERIALS

(75) Inventors: Enrique Iglesia, Moraga, CA (US); Laurent Kieken, Menlo Park, CA (US); Matthew Neurock, Charlottesville, VA (US)

(73) Assignee: NovoDynamics, Inc., Ann Arbor, MI (US)

( * ) Notice: Subject to any disclaimer, the term of this patent is extended or adjusted under 35 U.S.C. 154(b) by 34 days.

(21) Appl. No.: 09/921,929

(22) Filed: Aug. 6, 2001

(65) Prior Publication Data

US 2002/0086791 A1 Jul. 4, 2002

Related U.S. Application Data

(60) Provisional application No. 60/223,650, filed on Aug. 7, 2000.

(51) Int. Cl.[7] .............................................. G01N 31/00
(52) U.S. Cl. ............................ 702/22; 702/22; 702/32; 702/179; 702/182; 422/196; 422/197; 700/266; 700/268; 436/37; 436/85; 436/147; 436/159
(58) Field of Search ........................ 702/22–24, 30–33, 702/50, 179, 182, 183, FOR 115, FOR 119, FOR 121, FOR 134, FOR 139, 170; 436/37, 85, 147, 148, 159; 435/DIG. 22, 29, 30; 422/197, 196, 198; 700/266, 268

(56) References Cited

U.S. PATENT DOCUMENTS

| | | | |
|---|---|---|---|
| 5,774,381 A | | 6/1998 | Meier |
| 6,373,570 B1 | * | 4/2002 | McFarland et al. .......... 356/364 |
| 6,489,168 B1 | * | 12/2002 | Wang et al. .................... 436/37 |
| 2001/0034064 A1 | * | 10/2001 | Turner et al. ................... 436/34 |
| 2002/0098471 A1 | * | 7/2002 | Weinberg et al. ............... 435/4 |

FOREIGN PATENT DOCUMENTS

EP 1 089 205 A2 4/2001
WO PCT/US02/05046 2/2002

OTHER PUBLICATIONS

U.S. patent application Ser. No. 60/223,650, Iglesia, filed Aug. 7, 2000.

Smith, et al.: "Kinetic Modelling of Higher Alcohol Synthesis over Alkali–Promoted Cu/ZnO and MoS2 Catalysts" Chemical Engineering Science, vol. 45, No. 8, 1990, pp. 2639–2646 (Abstract).

Kito, et al.: "An Expert Systems Approach to Computer–Aided Design of Multi–Component Catalysts" Chemical Engineering Science, vol. 45, No. 8, 1990, pp. 2661–2667 (whole Document).

Trimm, David L.: "Chemical Engineering Monographs" (S.W. Churchill (Ed.)) vol. 11: Design of Industrial Catalysts, Elsevier, Amsterdam, NL 1980, p. 3, p. 36.

Happel, et al.: "Multiple Reaction Mechanisms in Catalysis" Industrial and Engineering Chemistry Fundamentals, American Chemical Society, Washington, US, vol. 21, No. 1, (Feb. 1982), pp. 67–76, (Whole Document, especially Paragraph 7 (Conclusions)).

* cited by examiner

Primary Examiner—Marc S. Hoff
Assistant Examiner—Elias Desta
(74) Attorney, Agent, or Firm—James M. Singer; Pepper Hamilton LLP (57) ABSTRACT

A method and system for the development of materials includes a high-throughput data-generation cycle, a knowledge-generation cycle, and a knowledge repository or database. The data-generation cycle generates high-quality data for the virtual and experimental evaluation of new catalytic materials. The knowledge-generation cycle generates working hypotheses, relating performance to catalyst properties, from analysis and modeling of experimental and virtual data and data from literature, from correlations generated from experimental, theoretical, and/or modeling findings, and optionally from computational chemistry modeling investigations, in order to identify better materials.

9 Claims, 2 Drawing Sheets

KNOWLEDGE-BASED PROCESS FOR THE DEVELOPMENT OF MATERIALS

PRIORITY

This application claims priority to the provisional U.S. patent application entitled, Knowledge-Based Process for the Development of Materials, filed Aug. 7, 2000, having a Ser. No. 60/223,650, the disclosure of which is hereby incorporated by reference.

FIELD OF THE INVENTION

The present invention relates generally to materials, and, more particularly to a process for the rational development of materials used in chemical processes, including but not limited to heterogeneous catalysts. This novel process when applied to heterogeneous catalysts is referred to as a catalyst development engine.

BACKGROUND OF THE INVENTION

The still emerging, recent application of combinatorial chemistry to high-speed high throughput synthesis and screening of materials does not adequately address the commercial requirements that a catalyst must meet. Current combinatorial methods are based on random screening of large libraries of materials, prepared and evaluated under unrealistic conditions that are difficult to scale up. Thus, little useful knowledge is derived from such experiments to guide the selection of the next set of experiments or materials. In order to reduce the time to market for new catalysts and processes, the catalysts must be synthesized using scalable methods and evaluated under real-world conditions as quickly as possible.

Thus, there is a need in the art to rapidly and efficiently identify routes to new materials by using computational (modeling) and high-throughput (HTP) synthesis and evaluation methodologies.

SUMMARY OF THE INVENTION

The present invention satisfies this need by providing a system and method to rapidly and efficiently identify routes to new materials by using computational (modeling) and high-throughput (HTP) synthesis and evaluation methodologies. These methodologies are integrated under a powerful informatics umbrella package that optimizes learning and knowledge.

Additional advantages of the invention will be set forth in part in the description which follows, and in part will be learned from the description, or may be learned by practice of the invention. The advantages of the invention will be realized and attained by means of the elements and combinations particularly pointed out in the appended claims.

In accordance with the purpose of the invention, as embodied and broadly described herein, the invention comprises a process for providing a rapid approach to the rational development of scalable high-performance materials used in chemical processes, the process including: (a) a high-throughput data generation cycle for rapidly generating informative data in a high-throughput mode for virtual and experimental evaluation of new materials; (b) a knowledge generation cycle that uses input from existing experimental data, correlations generated from experimental, theoretical, and/or modeling findings, theoretical and modeling investigations and the combination thereof in order to generate: (i) working hypotheses and (ii) suggested steps for experimental and/or theoretical investigations to guide the search for better materials; (c) a knowledge repository for storing the data generated by the high-throughput data generation cycle and for storing the knowledge generated by the knowledge generation cycle; and (d) a software/hardware platform that integrates the high-throughput data generation cycle with the knowledge generation cycle.

It is to be understood that both the foregoing general description and the following detailed description are exemplary and explanatory only and they are not in any way restrictive of the invention, as claimed.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings.

DETAILED DESCRIPTION OF PREFERRED EMBODIMENTS OF THE INVENTION

Reference will now be made in detail to the present preferred embodiments of the invention, examples of which are illustrated in the accompanying drawings. Wherever possible, the same reference numbers will be used throughout the drawings to refer to the same or similar parts.

Reference will now be made in detail to the present preferred embodiments of the invention, examples of which are illustrated in the accompanying drawings. Wherever possible, the same reference numbers will be used throughout the drawings to refer to the same or similar parts.

I. Introduction

The present invention may be applied to the development of new heterogeneous catalytic systems requires two stages: Phase I, the tool and infrastructure development; and Phase II, the catalyst development program.

A. Tool and Infrastructure Development (Catalyst Development Engine™)

The present invention was derived by first testing and validating computational methods for modeling heterogeneous catalysts, and developing the data and knowledge management systems. The technology (hardware, software, robotics) for HTP syntheses of heterogeneous catalysts and the methods for equipment use were then developed. Finally, the technology (hardware, software, and robotics) for the HTP evaluation of vapor-solid phase reactions involving heterogeneous catalysts was developed, including the development of methods for measuring key catalyst properties and catalyst performance.

B. Catalyst Development Program

As an example, the Catalyst Development Engine™ is applied to the development of an NO decomposition catalyst. The catalyst development program first involves identifying potential NO decomposition catalysts with suitable activity. The decomposition of the NO component (the dominant $NO_x$ component) in an exhaust stream into nitrogen and oxygen is the target reaction. Catalytic materials that can accomplish this task under realistic evaluation conditions have an excellent chance of being commercially viable. The next step of the process includes performing iterations of the computational/HTP synthesis and evaluating methods developed in Phase I to identify the better performing materials and optimize NO decomposition catalyst performance.

The final step of the process entails transferring the promising catalysts into a formal development and commercialization program. This step is commercialization-oriented. The point of transfer will depend on how much support work will be required in the preparation of the prototype catalyst pieces for more accurate evaluation under actual automotive operation conditions (e.g. long-term life testing to determine the commercial viability).

II. Phase I: Tool and Infrastructure Development (Catalyst Development Engine™)

This section provides an overview of the Catalyst Development Engine™ of the present invention and discusses the tools and methods development required for catalyst selection, synthesis and evaluation, covering (1) computational methods and, informatics system, and (2) HTP equipment and methods.

Figure 1:
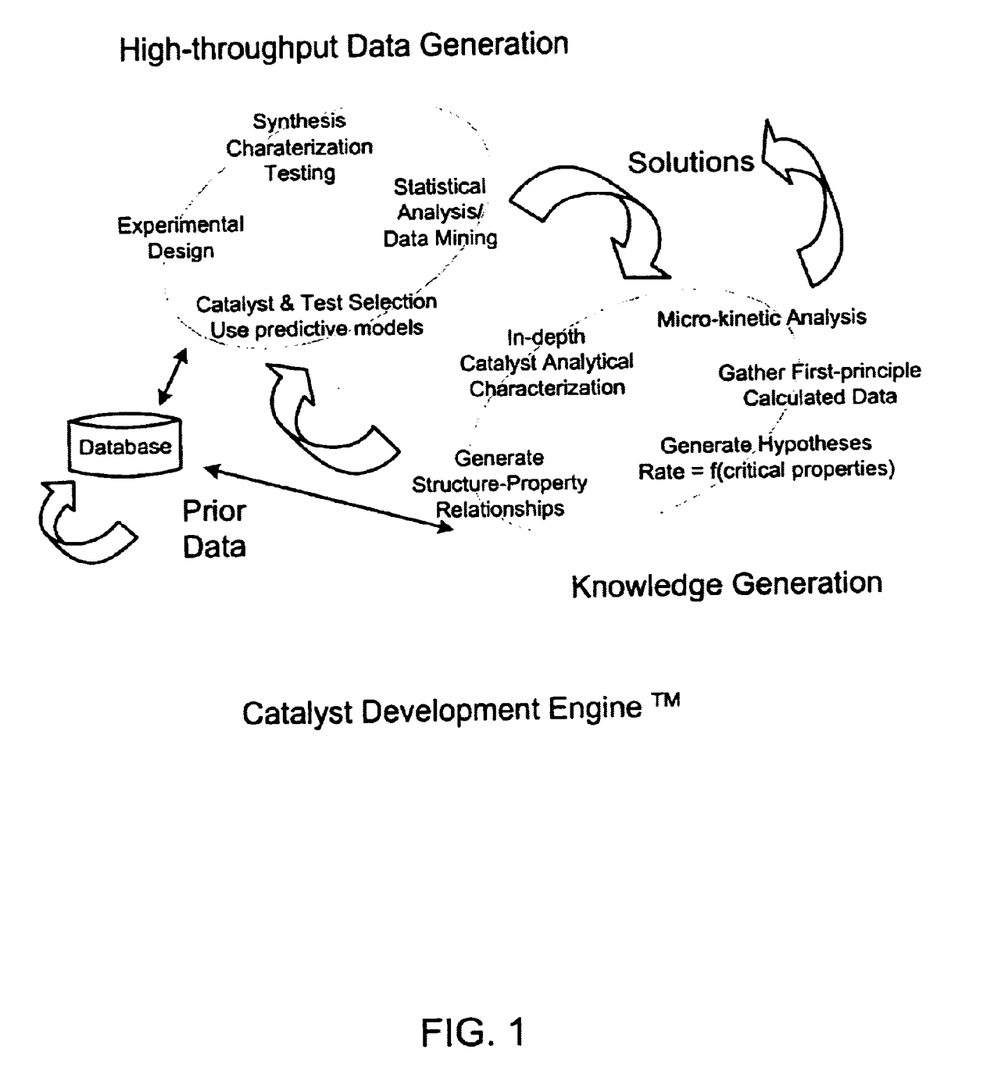
FIG. 1 is a schematic diagram showing a catalyst development engine of the present invention.

The topics discussed under this heading are the key components of the novel Catalyst Development Engine™ depicted in FIG. 1. The engine provides a rapid approach to the rational development of scalable heterogeneous catalysts and of high-performance solid materials. The catalyst development engine consists of three main components that are intimately connected in an integration framework: the high-throughput data generation cycle, the knowledge generation cycle, and the knowledge repository (database). The primary function of the high-throughput data generation cycle is to rapidly generate informative data in a high-throughput mode for the virtual and experimental evaluation of new catalytic materials and also generate data on well-characterized systems and for probe reactions of materials properties such as, but not restricted to, acidity, basicity, reducibility, etc. for use in the knowledge generation cycle. The primary functions of the knowledge generation cycle are (1) to generate working hypotheses relating performance to key catalyst properties that will guide the search for even better catalysts and (2) to generate fundamental structure-property relationships that will be instrumental in the selection of catalysts for further experimental evaluation in the high-throughput cycle. Both cycles run concurrently and feature theoretical and experimental activities that are highly integrated. Catalyst synthesis uses methods such as impregnation, precipitation, and others that are used commercially. Catalyst evaluation generates kinetic data that can be used in the knowledge cycle, and under commercially representative conditions. The knowledge repository expands with each iteration through the cycles. The knowledge repository includes materials properties and catalyst performance data for a comprehensive database of materials and for characteristic probe reactions of materials properties. Such an approach accelerates development and scale-up of new materials without the impediments introduced by conventional combinatorial approaches based on randomly selected materials prepared under unrealistic and difficult to scale up conditions.

The components and activities of the Catalyst Development Engine™ are described in more detail in the next paragraphs.

The Catalyst Development Engine™ includes several steps. They include: (1) a Statement of the Problem; (2) a High-Throughput Data-Generation Cycle; and (3) a Knowledge-Generation Cycle 1. Statement of Problem: The Statement of the Problem entails a concise statement clearly defining project goal(s) in terms that can be reasonably and adequately addressed with the tools available. All pertinent available data, independent of source, is collected, evaluated and stored in the knowledge repository in a format that is usable in the Catalyst Development Engine™.

2. High-Throughput Data-Generation Cycle: In this cycle, the emphasis on a rapid selection, preparation, and evaluation of potential catalysts. Semi-empirical calculation methods are used to assist in guiding the selection of catalyst targets to be evaluated. Data is mined for correlations to maximize learning. Features include:

a. Catalyst & Test Selection: The catalyst targets are selected for evaluation, which includes determining what performance tests are meaningful, e.g. rate, selectivities, conversions, heats of adsorption, etc. Semi-empirical and ab initio computational methods are used to narrow selection of catalyst systems to be tested based on key properties identified in the knowledge cycle.

b. Experimental Design: The catalyst(s) selected are prepared and evaluated according to an experimental design matrix. This ensures that the significant variables are effectively examined with the minimum number of experiments, while maximizing the information gathered.

c. Synthesis, Characterization and Evaluation: The catalysts are prepared using validated methodologies and HTP tools. They are characterized and evaluated for key properties and performance as prescribed by the experimental design.

d. Statistical Analysis/Data Mining: Experimental data is analyzed to test and refine the hypothesized performance-property relationships derived in the knowledge cycle. The use of statistical algorithms such as genetic algorithms and/or neural networks is used, to construct a learning model that can uncover patterns in the theoretical and experimental data. Data are mined for potential correlations between synthetic parameters, other macroscopic properties and surface properties that can guide experiments.

3. Knowledge-Generation Cycle: This cycle uses the information generated in the literature, in the HTP data-generation cycle for well-characterized systems, and from theoretical ab initio models to (1) evaluate possible reaction elementary steps postulated by microkinetic modeling; (2) identify key catalyst surface properties that affect performance; and (3) derive theoretical structure-property relationships to guide catalyst search. Features include:

a. Microkinetic Analysis: Microkinetic modeling is used to narrow the list of plausible reaction mechanisms that will be investigated by molecular modeling. Rate constants for elementary steps are estimated using calculated and measured parameters. Mechanisms that can reproduce general trends in existing data are studied in detail in the next step with molecular modeling.

b. Gather First-Principle Calculated Data: Ab initio computational models for selected catalysts are constructed and used to evaluate elementary steps of plausible mechanisms and calculate corresponding kinetic parameters.

c. Generate Hypothesis: Experimental and theoretical data on well-characterized catalyst systems are analyzed to generate hypotheses relating identified key catalyst properties (e.g. binding energies, activation energies, other surface properties) with kinetic parameters (and thus performance) of identified key elementary steps.

d. Generate Structure-Property Relationships: Electronic structure, composition/structure, particle size, support, and promoters can affect the surface properties of catalysts. Developing trends with theoretical models that relate key surface properties to these parameters will assist the scientist with deciding what "knob" to turn in order to tune the catalyst properties.

e. In-depth Catalyst Analytical Characterization: Selected experimental catalyst systems, which are also evaluated theoretically for the development of hypotheses and structure-property relationships, are well characterized for validation and refinement of models.

The Catalyst Development Engine™ may perform several iterations, and using the knowledge gained about the catalyst from the current cycle, it is determined how to proceed; either by preparing another round of targets based on the knowledge generated or by terminating this phase of the project because the catalyst meets the project goals or it is a dead end and the project continuation will be evaluated.

When a new catalyst that meets the performance criteria is identified, it is considered for scale-up and commercial development (in collaboration with partners and via conventional methods).

A. Computational (Modeling) Methods and Informatics System Development

The computational and informatics based approach outlined in Table 1 requires the selection and input of significant data as applied to the experimental and modeling problem being addressed and the storage of the resulting knowledge for its efficient future use. This has been a bottleneck and an ongoing problem for conventional one-at-a-time discovery and development systems based on randomly selected compositions prepared under unrealistic and difficult to scale up conditions. This section approaches this problem by describing the computational modeling methods that are suitable for treating heterogeneous catalyst problems and the data and knowledge management systems needed to make the Catalyst Development Engine™ approach viable.

1. Computational (Modeling) Methods

A predictive model is created which consists of two parts: an "ensemble hypothesis" and a Virtual Library. Based upon statistical analysis of known data sets (e.g. heterogeneous catalysts), a set of predictive hypotheses is determined and subsequently tested again on holdout data. In addition, state-of-the-art molecular modeling capability (including ab initio and semi-empirical methods) is used to help elucidate detailed structural effects. Meanwhile a Virtual Library—a database containing the knowledge related to the synthesis and detailed performance characteristics of the catalysts—will be created. The refined hypotheses is used to select promising candidates from the Virtual Library for synthesis.

Current state-of-the-art molecular modeling of catalysts involves either ab initio quantum chemical methods or semi-empirical methods. Ab initio quantum chemical methods are first-principle solutions to the Schrödinger equation, which make only a few very basic approximations. Because of the high level of detail and accuracy, they are applicable to essentially any material system but they require high computational intensity. They provide the best accuracy for a wide range of chemical and catalytic properties. These methods are used to examine the chemisorption and reactivity of all reactants, intermediates, and products at different surface coverages in order confirm the reaction mechanism and provide the parameters necessary for detailed microkinetic models (adsorption energies, activation energies, rate constants). In addition, a large set of chemical and catalytic properties for different catalytic systems are evaluated in order to develop a set of property libraries that are used to establish correlations (metal-adsorbate bond strengths, site acidity, site basicity, oxidation potential, etc.) and hypotheses tests.

Semi-empirical methods include both empirical theoretical models, such as Bond Order Conservation, and semi-empirical quantum chemical methods. Semi-empirical quantum chemical methods attempt to minimize the computational efforts of solving the Schrödinger equation by approximating computationally-limiting multi-center integrals. These approaches range from very approximate calculations such as extended Hückel calculations, which simply ignore the contributions from multi-center integrals, to very approximate methods using low computational times on the order of a few minutes. More sophisticated methods treat the multi-center interaction integrals using empirical information. They typically use experimental data or ab initio results in order to parametrize the integrals.

In terms of ab initio methods, Density Functional Theory (DFT) calculations provide the state-of-the-art for modeling catalytic systems and they can be used to predict chemisorption energies, overall reaction energies, activation barriers, and chemical properties descriptors which target key catalytic properties, such as acidity, basicity, and reducibility. Gradient-corrected DFT methods have proven to be the most robust and accurate methods for the prediction of large transition-metal systems due to their ability to explicitly treat electron correlation. The active surface sites can be approximated by using either a metal cluster model to represent the coordination and bonding of the active metal particles or a periodic slab model that represents larger exposed surfaces. The accuracy of DFT methods in predicting energetics for transition metal systems is +/−5 kcal/mol. Although quantitative accuracy is important, the ability to predict the relative trends across the periodic table is more critical for the identification of useful catalyst targets. This enables scanning of a range of unknown systems for optimal metal-adsorbate bond strengths and surface reactivity.

Recent studies have shown how these detailed calculations can be used to understand and predict the trends in both chemisorption and surface reactivity across the periodic table. Non-local cluster and periodic slab DFT calculations are used to compute the binding energies of maleic anhydride on the 111 surfaces of Pd, Re, Au, Pd/Re, Pt, Pd/Mo, and Pd/Au. Basic concepts from frontier molecular orbital theory are subsequently used to construct a general model that is able to predict a priori the outcome of the more detailed ab initio calculations. These models provide an understanding of the controlling factors that govern chemisorption as well as a knowledge-driven approach to the screening of multimetallic and metal oxide systems by simply computing a particular chemical descriptor (in this case the center of the d-band at the surface layer of the metal). This model is further extended to predict activation barriers for different elementary steps in the overall catalytic path. As such, studies show that the reactivity of the surface scaled with the relative location of the d-band center of the metal with respect to the Fermi level. Also, the reaction kinetics over different (111) surfaces is found to correlate quite well with changes in the center of the d-band. There is an optimal trade-off between different reactions. As the metal-adsorbate bond becomes too weak it becomes difficult to dissociate hydrogen on the surface. This shuts down the overall reaction.

While first-principle DFT is appropriate for establishing the reaction mechanism, and for accurately calculating properties for a large number of systems, the calculations still require 1–2 days per chemisorption evaluation. In order to offer daily guidance and be able to lead high-throughput screening efforts, a much faster method needs to be developed. The present invention uses a variety of semi-empirical methods that run for a few minutes to determine specific catalytic properties within reasonable accuracy. These methods are driven by technical staff coupled with advanced learning methods (genetic algorithms, neural nets) in order to develop a potential set of lead systems which meet the target properties.

More specifically, the present invention uses a modified version of the Atomic Superposition Electron Delocalization Molecular Orbital Theory (ASED-MO). ASED has been used by Anderson, van Santen, and others to describe many qualitative features and in some cases even quantitative assessments in catalysis. The applicability and accuracy of the approach depends on developing appropriate parameters. Much of this has been ad hoc by different individual groups, which have used limited experimental data to help parametrize the model. The present invention generates very detailed ab initio libraries as well as empirical databanks, which can be used to parametrize these systems more accurately. By way of simple comparison, we examined how well we could do in terms of producing trends by comparing simple ASED calculation which were optimized to detailed DFT calculations and found that the results show the correct trends to within 30% for NO, O, and N binding energies over a set of different metals. The application of structural optimization as well as refined regression of the parameters should improve the accuracy to 10–20%.

In addition to refined ASED models, the present inventors developed a more approximate Bond-Order Conservation (BOC). While BOC has some ties back to quantum chemical descriptions of bonding, it is a very simple approach that does not attempt to solve the Schrodinger equation. E. Shustorovich, *Metal-Surface Reaction Energetics*, VCH (1991) demonstrates that the approach offers some predictions to reactivity. The present inventors have found that some of the known shortcomings of this method can be overcome by determining interaction parameters from first-principle DFT methods. Also, tight binding or single-SCF DFT methods are used and evaluated for the most appropriate compromise between accuracy and speed. All software programs are available in house or commercially (molecular Simulations, Inc., Wavefunction, Inc.). The present invention uses NO decomposition as an example for the application of the methodology and the coordination of the data input and output with the informatics system.

2. Informatics and Database Development

The informatics system consists of data management and knowledge management systems bound together in an integration framework. The requirements for the data management system fall into six categories: (1) data acquisition, (2) data reduction, (3) data mining, (4) data visualization, (5) data archival/retrieval, and (6) communication protocols. These functions consist of hardware and software components. The hardware is available commercially. Most software items such as databases, data mining software, modeling software, are available commercially, others such as adapters, which allow communication of networks with instruments, requires programming that depends on individual instruments. A wide variety of information is recorded, tracked and analyzed in this system.

Record-keeping of synthesis and pre-treatment protocols: Reaction vessels are barcode labeled and synthesis procedures recorded. This includes specific data recorded for each vessel for the preparation of a supported catalyst, including tare weight, weight of support, support properties, array location (rack or holder), salt solution(s), stoichiometry, mixing time, reaction temperature, drying time and temperature, calcination time and temperature, and any other relevant variables and comments.

Handling by automated equipment: Barcodes may be used to identify racks, listing their contents and linking the history of that vessel.

Recording analytical and evaluation data: Data generated is stored in a database, so the researcher can review the catalyst synthesis history, evaluation results, and characterization data.

Recording theoretical data: Computational data is recorded and stored, including rate constants for elementary steps, binding and activation energies, and other properties for model materials, as well as structure-property relationships.

Knowledge system: The catalyst development engine is based on valuable catalyst and reaction knowledge and an understanding that is used to solve catalytic problems. Easy access, retrieval, and archival of this knowledge improves the decision-making ability and productivity of the process. The knowledge system is the information retrieval system that integrates multiple information sources and interfaces in a logical fashion. The information sources include experimental data, modeling, and theoretical data, literature, and information from proprietary corporate files. This information may be textual, numerical, structural, or logical, and may reside internally or remotely from the database. A knowledge repository structure may be designed for the catalytic scientist, which includes and integrates the various information databases and links it securely to the data management system, as well as to the Internet.

The advantages of the present invention are many. The ab initio/DFT computational models provide fundamental information on the elementary steps, focusing on key properties of the catalysts early on. The semi-empirical computational methods enable rapid analysis of a very large number of potential catalysts in a short time and at lower cost, permitting use of the present invention as a predictive tool rather than to merely analyze past results. The data available from the HTP cycle for "active" as well as "inactive" catalysts vastly expands the knowledge database and improves the quality of predictions. The informatics system allows rapid and effective management of information so as to decrease the labor and time intensity of data handling. This will permit the scientists to focus on the key technical issues related to the catalyst problem being addressed and to assist them in making decisions. The iterative approach also permits the rapid and continuous refinement of the predictive model.

HTP Equipment and Methods

HTP Catalyst Synthesis and Characterization

Equipment Development for Catalyst Synthesis and Characterization: The successful design and implementation of the HTP system requires significant innovations in order (1) to provide scalable and reproducible materials and (2) to integrate efficiently the synthesis and evaluation systems. A significant challenge is to automate and parallelize commercial catalyst synthesis to produce scalable and reproducible materials. The present invention uses highly controlled robotics and fluidics processes to produce high quality, reproducible materials with minimal human error. The design of the systems are based on unit operations common to the preparation of a broad range of heterogeneous catalysts, including non-refactory solids and supported metals and alloys. The design is scaled to obtain approximately 0.1–10 grams (g) of isolated catalyst per preparation.

Catalyst preparation relies on the use of synthesis modules, interfaced with drying ovens and calcination furnaces. One exemplary option for such a system is a novel reaction vessel design that allows synthesis, purification, drying and post-thermal processing without the need for time-consuming vessel transfers. Integration into a reactor vessel array provides a synthesis/processing cassette (SPC) which can be readily utilized in automated and manual processes with tracking controls. The synthesis module has the capability to quantitatively dispense liquid and solid reagents to multiple SPCs. Agitation during deliveries, on-line monitoring of critical reaction parameters, temperature control and purification is also included in the design. The module enables the synthesis of catalysts by precipitation, impregnation, solid state, or sol-gel techniques. A major innovation in the synthesis module includes the reactor vessel design to accommodate the spectrum of unit operations involved in catalyst preparation. The materials of construction for the reaction vessel meet the full spectrum of requirements to perform catalyst synthesis, purification, and thermal processing. Several materials may be investigated in the feasibility stage to afford the best balance of properties. The difficulties associated with accurate solids delivery and agitation of high solids mixtures in the synthesis module represents a significant departure from known automated synthesis platforms, which primarily handle solutions. Although, the intent is for a high level of automation, each unit operation will be evaluated and where appropriate semi-automated or manual tools may be developed if deemed more effective.

Methods Development for Catalyst Synthesis and Characterization: As catalyst families are selected for high-throughput synthesis, they are prepared in a 0.1–10 g scale to provide the quantity of material required for testing, characterization and archival. The products are carefully characterized to ensure that their composition and structural features are as specified. The time required for this can be extensive, because each step must be compatible with the HTP synthesis equipment and its limitations and requires the dedicated effort of a team of chemists working in conjunction with the designers of catalyst evaluation equipment.

Emphasis in this example is placed on both incipient wetness impregnation and co-precipitation methods for the synthesis of supported metal and mixed metal oxide catalysts, because these materials in pure or modified form are used in the NO decomposition catalyst evaluations. The methods for in-house catalyst preparation using HTP synthesis may need to be developed to ensure that the materials synthesized are those intended and that the preparations are reproducible. The refinement of the synthesis module in conjunction with the development of reliable methods, ultimately leads to accelerated synthetic route development. Since most compositional and structural characterization methods are lower throughput than the HTP synthesis/evaluation system, only a subset of the samples prepared will, in general, be fully characterized.

C. HTP Catalyst Evaluation

1. Equipment Development for Catalyst Evaluation

The present invention uses a reactor system that enables gathering of kinetic information on powdered catalysts without corruption by transport restrictions. The reactor system enables evaluation of several catalysts (4–24 per module) under identical and commercially relevant reaction conditions, as well as evaluation of the same catalyst under various process conditions. The present invention has the capability to synthesize and evaluate approximately 150–300 catalysts per week or 7,500–15,000 per year. The actual capability will depend on the catalyst type (synthesis requirements) and the evaluation reaction condition requirements.

For maximum flexibility in applications, the present invention uses a modular approach, whereby the catalyst synthesis, testing, and analysis operations are performed in separate modules, which are combined to automate the majority of the process. Although the HTP equipment is used initially for NO decomposition catalysts, it is designed for adaptation to other vapor-solid and possibly vapor-liquid-solid applications. In the feasibility phase of the catalyst evaluation module, the design and materials choices are made that allow adaptation to configurations that enable the use of a vapor-solid fixed bed from atmospheric to elevated pressures.

A catalyst evaluation module integrates with vessels utilized in synthesis and archival. The robotic solids handling, precision delivery, and weighing capability of the synthesis module are leveraged into other product areas for the quantitative transfer of catalyst from the reaction array to the microreactors. In the case of precipitated catalysts, pelletizing, grinding and sieving are accomplished with a new set of manual tools that are developed to provide the correct particle size (60–100 mesh) for catalyst studies and more uniform solids delivery. Once charged, the flow reactors can be inserted into the testing tool for catalyst pretreatment and kinetic evaluation.

Figure 2:
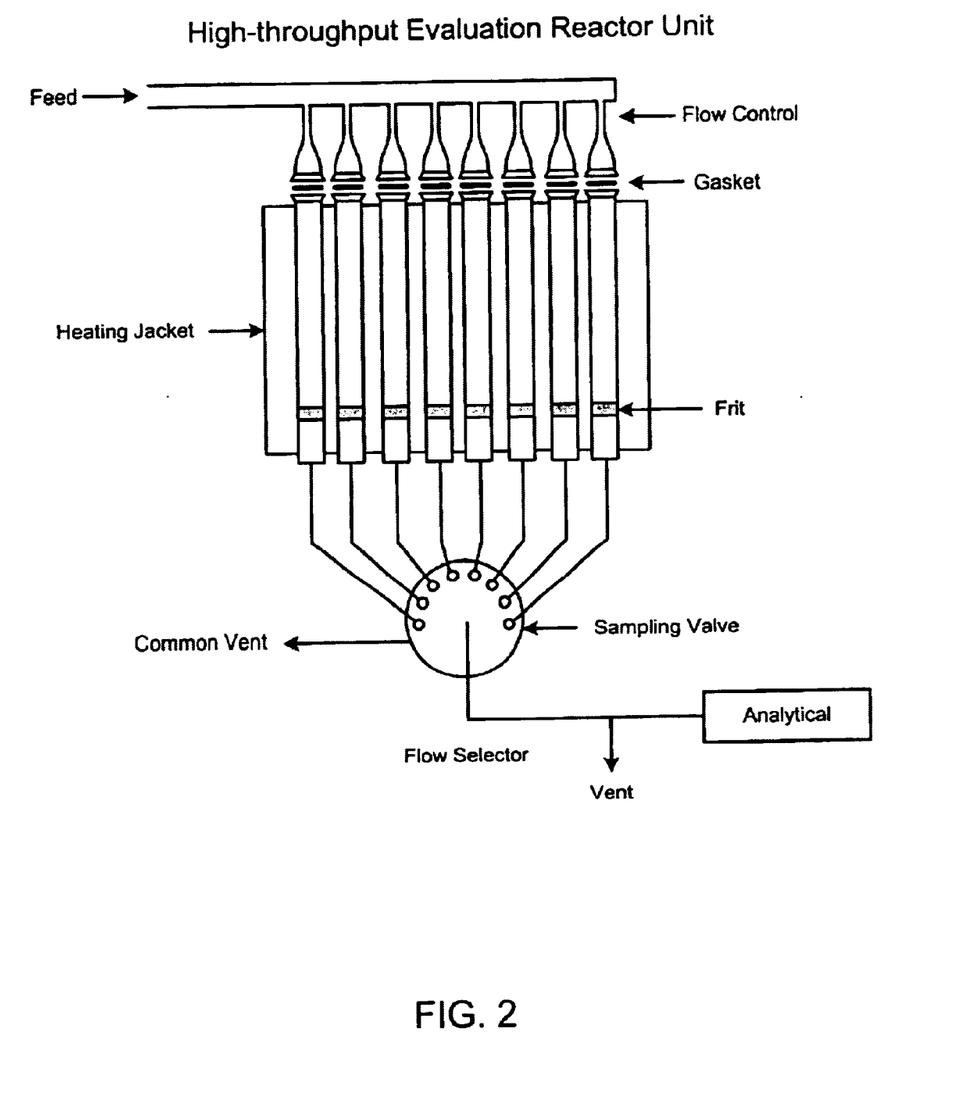
FIG. 2 is a schematic diagram showing a high-throughput evaluation reactor unit of the present invention.

A general design for the catalyst-testing module is shown in FIG. 2. It consists of a series of 4 to 24 parallel fixed-bed microreactors. These reactors are connected through the use of an insulating coupon(s) to allow them to be handled as an integrated unit, or microreactor cassette (MRC). The innovative design strives for rapid connection of feed and product lines through the use of connection blocks for easy insertion of the MRC. An autosampler can be used for unattended switching of MRCs. The materials of construction for the microreactor unit are an important choice and several materials may be used, including stainless steel, ceramic and quartz. Requisite material properties include the ability to achieve high temperatures and high pressures, depending on the specific application. The use of different materials for specific application regimes may be employed.

A common cycle used in catalyst evaluation involves pretreatment, establishing steady state conditions, and sampling the streams of each reactor in turn. Upon completion of the analysis sampling cycle, the reaction parameters are changed to the next programmed setpoint and the process repeated. It is anticipated that the kinetics of NO decomposition on a MRC charged with catalysts can be measured within a 4 to 6 hour period. Through automation of the switching of the MRCs a throughput of 30–50 samples/day is anticipated.

The reactor tube inner diameter is approximately 0.3 cm. The catalyst average particle size should be consistent with the dimensions of the screening fixed-bed reactor to avoid transport limitations. Catalyst average particle size should be in the range of 60–100 mesh. Given a catalyst bed 0.3 cm in diameter and a minimum of 1 cm in length, the necessary catalyst quantity is estimated at 10–100 mg, which is well within the target quantity of material to be synthesized.

The MRCs permit temperature control of each individual microreactor unit with a heating jacket having a temperature range of 20–800° C. Insertion of the MRC in the catalyst-testing module establishes the necessary contacts for heater control and temperature monitoring.

Mass flow controllers are used to control the flow rate of a gas mixture to a reactor unit for material pretreatment or reaction. The gas flow is then split between the reactors. The system enables individual adjustment of the feed rate for each reactor. This provides advantages for precisely specifying the space velocity of feed gases for the measured catalyst amount and extension of the system to more complete testing of a single catalyst that has been identified as a promising candidate. The outlet of the MRC is connected to a sampling system, described below.

The design of the sampling system and the choice of analytical instrumentation is made with emphasis on the specific NO decomposition catalyst application chosen as an illustration. The outlet of each MRC is coupled with a multiport valve, via a low-dead-volume line, to allow for sampling of the outlet gas from each reactor successively. A quadruple mass spectrometer (QMS), fast gas chromatography and/or Raman spectroscopy are used to determine overall conversion and selectivity of the catalytic material. Complementary techniques are desirable because of the difficulty in analyzing small amounts of $NO_2$ in low volume gas streams.

The QMS is connected to the sampling valve via a capillary that may be heated if required to avoid condensation. A QMS is best suited for this gas analysis because it has a fast response time (only a few seconds), high accuracy, requires low sample volumes, allows for on-line analysis, and is chemically selective. The QMS is calibrated with known composition reference gases to determine absolute concentrations of $N_2$, NO, $N_2O$ and $NO_2$. The overlapping patterns at m/e=28 and 30 is calculated using deconvolution methods. The number of parallel gas streams (i.e., reactors) analyzed with one QMS depends on analysis time. Analytical instrumentation supplier options include Stanford Research Systems, Agilent Technologies and Finnigan, and Balzers. In addition to the use of QMS, Raman spectroscopy may be used as an independent technique to quantify NO, $N_2O$, and $NO_2$ to ensure mass balance. In order to achieve fast, on-line analysis a novel waveguiding technique for sampling may be used. The system may include a single waveguide multiplexed to the streams. With this arrangment, acquisition times of less than a minute per sample are achievable.

2. Methods Development for Catalyst Evaluation

The methods development involves developing viable experimental methods for evaluating the catalyst samples in the HTP vapor-solid reactor described above so that the data obtained are reproducible and valid. To accomplish this a series of standards are examined using both manual and automated procedures. The standards are not only selected because that they are well-known and characterized but also because the data collected from them are of value to the program once the reproducibility and validity of the system have been confirmed.

Outside sources of commercially viable materials may also be evaluated in the discovery and development program. Catalyst evaluation is performed when the materials obtained can sufficiently provide useful knowledge. The use of samples derived from commercial sources such as nano-materials prepared by unique methods that do not lend themselves to synthesis in the HPT equipment, e.g. sputtering or flame generation methods, has the benefit of material availability. If the material is successful there is a much better chance of obtaining it in commercially meaningful quantities and at a reasonable price.

III. Phase II: Catalyst Development Program

The computational/HTP Catalyst Development Engine™ is used to identify and optimize commercially viable NO decomposition catalysts for use with lean-burn (spark ignition direct injection) SIDI engines. These new catalysts enable the rapid large-scale commercial use of lean-burn engines and the realization of associated economic and environmental benefits. Currently, catalytic converters for traditional combustion engines are based on three-way catalysts (TWC's), which are incompatible with lean-burn engines. Despite extensive R&D efforts to date, catalytic converters for lean-burn SIDI engines are not yet practical for commercial use The key technical barrier for a viable catalyst seems to be the higher affinity of oxygen for the catalytic site relative to the minority NO component—site competition. Since oxygen is present in much higher concentrations, the rate of NO decomposition is too slow to be commercially viable. NO decomposition is thermodynamically favored over a wide temperature range of practical interest and the only reaction products are nitrogen and oxygen. The goal of the example of the present invention is aimed at preparing NO decomposition catalysts that overcome the limitations of current catalysts and would be viable for commercial use.

A. Review of Past Catalyst Results

Despite extensive research efforts over the past 10–12 years, the currently known catalysts that decompose NO under the oxygen-rich conditions of the lean-burn engine still have severe limitations preventing their commercialization. These limitations include low activity, inhibition by high oxygen levels, poisoning by oxides of sulfur ($SO_x$), and inadequate hydrothermal stability. To put the required commercial catalyst performance into perspective, the average rate of NO decomposition (for a 80% removal level) needs to be $1.3 \times 10^{-4}$ mol g$^{-1}$ min$^{-1}$, calculated over the range of temperatures of operation (200–600° C.). This rate is about approximately 50 times greater than the estimated rate on the most active catalyst identified to date [Cu-ZSM-5 catalyst reported in Y. Li and W. K. Hall, *J. Catal.*, 129,202 (1991)].

Recently studied catalysts fall into three general categories: transition metals, complex metal oxides, and metal ion-exchanged zeolites. The present example focuses on the better, but still far from adequately-performing active cata lytic components. Table 2 presents an overview of some of the better performing catalysts from past work.

TABLE 2

Potential NO Decomposition Catalysts Evaluated

| Catalyst | Advantages | Disadvantages |
| --- | --- | --- |
| Cu-ZSM-5 (GM) | Appears to be active for both NO adsorption and decomposition | Poor hydrothermal stability - dealumination of the zeolite $SO_2$ poisoning |
| Fe-ZSM-5 | Appears to be active for both NO adsorption and decomposition | Poor hydrothermal stability - dealumination of the zeolite $SO_2$ poisoning $NO_2$ formation |
| Precious metals | Good hydrothermal stability Less sensitive to $SO_2$ poisoning | $NO_2$ formation |
| Pt/alumina | Less sensitive to $SO_2$ poisoning | $NO_2$ formation |
| Co oxide | | $SO_2$ poisoning |
| Fluorite and Brownmillerite (Eltron Research) | Up to 100% NO removal High concentration of O vacancies active for NO adsorption and decomposition | Seems to rely on exhaust gas CO and HC for NO removal Work done with no $O_2$ present |
| Perovskite | Molecular modeling study done with performance testing (Japan) | Low NO decomposition activity |
| $WO_3$ + Pt/alumina (Ford) | $WO_3$ has a positive effect on NO removal Test was done with $SO_2$ present | Best results were not up to desired 80% removal level Life information not reported Reduction may significantly contribute to NO removal since CO and HC are present |

Several companies are working to develop improved catalysts for NO decomposition but not all of them are being tested under completely oxidizing conditions. Ford has reported work on a $WO_3$-Pt/alumina catalyst that has fair NO decomposition activity but does not meet specifications. Eltron Research, Inc. has claimed new NO removal catalysts based upon modified oxygen-deficient fluorite or brownmillerite structures that are active for NO adsorption and dissociation. This work has given good results (100% NO removal) but the "decomposition" occurs via reduction using the CO and HC components in the absence of oxygen and not by actual decomposition to nitrogen and oxygen. In Japan, a collaboration of Japanese gas companies recently reported work on the modification of a perovskite catalyst, assisted by molecular orbital modeling, but so far the performance of the material developed is not of commercial interest.

The problem of hydrothermal stability affects most zeolite based catalysts, especially Cu-ZSM-5, as set forth in M. Iwamoto and H. Hamada, Catal. Today, 10, 57 (1991). The zeolite catalysts are active for NO decomposition but they are prone to dealumination and loss of crystallinity at high temperatures (above 973 K.) in the presence of water vapor (typically comprising 8–10% of the exhaust). Hence, Cu-ZSM-5 is unlikely to be stable enough to pass the durability test of the FTP (Federal Test Procedure), as set forth in J. N. Armor, Catal. Today, 26, 99 (1995). Furthermore, $SO_2$ poisons Cu-ZSM-5. Since the hydrothermal stability and poisoning problems of ZSM-5 based catalysts still exist despite extensive efforts to improve them, the present inventors did not investigate zeolite-based systems. However, the present inventors have studied Cu-ZSM-5 as a reference catalyst in the development of our models in order to understand the properties of the active Cu species.

Noble-metal catalysts are active, as evidenced by their proven performance in the TWCs, but they do not have sufficient NO decomposition activity for lean-burn engine application without serious modification. Supported noble-metal catalysts resist $SO_2$ poisoning better than Cu-ZSM-5 probably because of their ability to oxidize the $SO_2$ to $SO_3$.

It is likely that the catalysts evaluated for NO decomposition using exhaust gas model feeds having HC and CO components work by a combination of reduction and decomposition and this is acceptable for commercial operation. However, in this example of the present invention the goal is to meet the desired 80% removal of NO specification by using an oxygen-rich stream without CO, HC, or other reducing agent being present. If the NO specification can be met without the presence of reducing agents, then the catalyst would meet and probably exceed the standards with the reducing agents available in a live exhaust stream.

B. NO Decomposition Catalyst Development

Based on the literature information discussed in the last section, one hypothesis is that three types of active sites are possible for the catalytic NO decomposition reaction. Type 1 sites where NO has a high affinity for the metal centered catalytic site but the site does not catalytically decompose the NO molecule. Examples from the literature [J. Armor et al., J. Am. Chem. Soc., 90, 5928 (1968) and A. G. Wittaker and D. M. Yost, J. Am. Chem. Soc., 71, 3135 (1949)] include the stable $V^{4+}$ and $Ru^{3+}$ centered species where the NO is tightly bound to the metal center. These results seem to be influenced by the matrix in which the metal ion is located.

Type 2 sites are sites where $O_2$ has a higher affinity for the metal site than NO but the site is active for the catalytic decomposition of NO to $N_2$ and $O_2$. Examples of this type of site include Pd and Pt. These noble metals are good oxidation catalysts and this can lead to more complicated and offsetting chemistry such as the oxidation of NO to $NO_2$ and the oxidation of the potential catalyst poison $SO_2$ to $SO_3$.

Type 3 sites which can be thought of as a combination of Type 1 and Type 2 sites are sites where NO is selectively adsorbed over $O_2$ and the NO decomposes at a commercially feasible rate under reasonable conditions. Possible examples of these sites include $Cu^{2+}$ and $Fe^{2+}$ species either on supports or in matrices other than zeolites. $Ru^{3+}$ (mentioned in Type 1) may also fit here if placed into a different stabilizing matrix. The superior performance of ion-exchanged Cu-ZSM-5 suggests that Cu species may be in a bridged configuration.

The target would be to identify: (1) either a Type 1-Type 2 site combination that would permit the selective coordination of NO to a Type 1 site with spillover onto a Type 2 site, that has been modified to lower oxygen affinity; or (2) a Type 3 site that has the required selectivity for NO adsorption, decomposition and is stable to poisons such as $SO_2$.

To accomplish this the sites need to be constructed by selecting an appropriate active metal site, a matrix for the active metal and modifiers for improving the active sites activity and selectivity. The use of modifiers need not be addressed, but there is solid evidence to indicate that the use of modifiers such as Cu, Sn, Au and Ag can have a significant impact on the oxygen affinity. The desirable features of the active sites are outlined in Table 3 along with examples of potential metal species that may be suitable initial catalyst targets.

TABLE 3

Potential NO Decomposition Active Sites and Their Characteristics

| Site Type | Desired characteristics: | Anticipated required site features: |
|---|---|---|
| Type 1 sites Examples: $VO^{2+}$, $Cr^{3+}$, $Co^{3+}$, $MoO^{3+}$, $WO^{4+}$, and high oxidation state lanthanide's | Low $O_2$ adsorption Good but reversible NO adsorption to permit spillover to type 2 sites Resistant to $SO_2$ | Unsaturated site with easy access for NO Catalyst matrix with electron donor capabilities to modify the metal site to permit NO mobility Matrix that is hydrothermally stable |
| Type 2 sites Examples: Pd, Pt, and metals in general in their zero valent state | Decreased preference for $O_2$ adsorption on the unmodified site Increased NO adsorption and decomposition rate Resistant to $SO_2$ | Unsaturated site with easy access for NO Catalyst matrix with electron acceptor capabilities to modify the metal site to permit NO adsorption based on spillover from the type 1 site Matrix that is hydrothermally stable |
| Type 3 sites Examples: $Cu^{2+}$, $Fe^{2+}$, $Pt^{4+}$, $Ni^{2+}$, $Co^{2+}$, $Ru^{3+}$ | Single site that is highly selective to NO adsorption and decomposition Resistant to $SO_2$ | Properties need to be border line between type 1 and 2 sites as described Matrix that is hydrothermally stable |

It is encouraging that the catalysts discussed above in the review of past NO decomposition efforts seem to fall into the proper categories in this listing. Much work is still required to validate this hypothesis. However, the use of the Catalyst Development Engine™ will enable refinement of the hypothesis based on new experimental and theoretical data.

B. Catalyst Evaluation and Exhaust Stream Composition

Catalyst sensitivity studies need to be done for other exhaust stream components in conjunction with the site types and the simple pure feed studies. In particular the effect of $H_2O$ and $SO_2$ needs to be understood since these components have been shown to have a detrimental effect on NO decomposition catalyst performance. The potential effects of the key exhaust components have been considered while setting up the tasks for the present invention. Table 4 provides an overview of the exhaust components considered and their potential to influence NO decomposition.

TABLE 4

Testing Exhaust Stream Components

| Component | Potential effect on NO Decomposition | Testing for Effect |
|---|---|---|
| NO | Test as a pure feed and in mixtures | Yes |
| $NO_x$ | Only consider the formation of NOx from NO as part of this study and not its decomposition | No |
| $O_2$ | Test in high concentrations similar to those found in lean-burn engines. | Yes |
| HC | Elimination can be accomplished by oxidation to $CO_2$ using conventional technology. Use of HC's could bias the NO decomposition tests, since HG is a reducing agent and offers an alternate route for NO elimination. | No |
| $SO_2$ | Catalyst poison so catalyst resistance to $SO_2$ is of interest. | Yes |

TABLE 4-continued

Testing Exhaust Stream Components

| Component | Potential effect on NO Decomposition | Testing for Effect |
|---|---|---|
| CO | Elimination can be accomplished by oxidation to $CO_2$ using conventional technology. Use of CO could bias the NO decomposition tests, since CO is a reducing agent and it offers an alternate route for NO elimination. | No |
| $H_2O$ | Can influence catalyst and support hydrothermal stability | Yes |
| Particulates | Not a problem for gasoline engines and will not influence NO decomposition catalyst performance | No |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for providing a rapid approach to the rational development of scalable high-performance materials, the process comprising:

a high-throughput data generation cycle for rapidly generating informative data in a high-throughput mode for virtual and experimental evaluation of new materials;

a knowledge generation cycle that uses input from existing experimental data, correlations generated from experimental, theoretical, and/or modeling findings, theoretical and modeling investigations and the combination thereof in order to generate: (i) working hypotheses and (ii) suggested steps for experimental and/or theoretical investigations to guide the search for better materials;

a knowledge repository for storing the data generated by the high-throughput data generation cycle and for storing the knowledge generated by the knowledge generation cycle and its database content; and a software/hardware platform that integrates the high-throughput data generation cycle with the knowledge generation cycle.

2. The process of claim 1 applied to the rational development of scalable high-performance materials used in chemical processes.

3. The process of claim 1 applied to the rational development of scalable heterogeneous catalysts.

4. A computer-assisted method for developing materials, comprising:

identifying data that includes at least one of (i) input from existing experimental data; (ii) correlations generated from at least one of experimental, theoretical, and/or modeling findings; and (iii) theoretical and modeling investigations to generate working hypotheses; and based on the data identified in the identifying step, suggesting next steps for at least one of experimental investigations and theoretical investigations to identify better materials.

5. The computer-assisted method of claim 4 in which the identifying step further includes identifying the results of microkinetic modeling investigations.

6. The computer-assisted method of claim 4 in which the method further comprises:

selecting a data set for a set of materials, the data set comprising one or more dependent performance variables for a chemical process and independent variables;

building a model that correlates the dependent performance variables with one or more of the independent variables;

identifying one or more of the independent variables having values that yield improved values of the dependent performance variables based on the results of the model;

generating a next step for an investigation that measures or calculates the dependent variable associated with the improved values of the independent variables; and identifying from one of experimental and theoretical investigations one or more new materials that are associated with the values of the one or more independent variables that yield improved values of the dependent variables.

7. The method of claim 6 wherein the independent variables include calculated or measured properties of the materials or preparation parameters relating to the materials.

8. The computer-assisted method of claim 4 applied to the development of materials used in a chemical process.

9. The computer-assisted method of claim 4 used in the development of heterogeneous catalytic materials.

* * * * *